United States Patent [19]
Ollar

[11] Patent Number: 5,891,662
[45] Date of Patent: Apr. 6, 1999

[54] METHOD FOR DETERMINING THE ANTIMICROBIAL AGENT SENSITIVITY OF A NONPARAFFINOPHILIC HYDROPHOBIC MICROORGANISM

[75] Inventor: Robert-A. Ollar, Milford, Pa.

[73] Assignee: Infectech, Inc., Sharon, Pa.

[21] Appl. No.: 969,588

[22] Filed: Nov. 13, 1997

[51] Int. Cl.[6] ..................................... C12Q 1/18
[52] U.S. Cl. ................. 435/32; 435/30; 435/34
[58] Field of Search .................. 435/32, 34, 30, 435/29, 287.9

[56] References Cited

U.S. PATENT DOCUMENTS

| | | | |
|---|---|---|---|
| 5,153,119 | 10/1992 | Ollar | 435/34 |
| 5,316,918 | 5/1994 | Ollar | 435/34 |
| 5,472,877 | 12/1995 | Ollar | 435/288.1 |
| 5,569,592 | 10/1996 | Ollar | 435/32 |
| 5,637,501 | 6/1997 | Ollar et al. | 435/286.2 |
| 5,639,675 | 6/1997 | Felder et al. | 435/29 |
| 5,641,645 | 6/1997 | Felder et al. | 435/32 |
| 5,654,194 | 8/1997 | Felder et al. | 435/287.9 |
| 5,663,056 | 9/1997 | Ollar et al. | 435/29 |
| 5,668,010 | 9/1997 | Felder et al. | 435/287.9 |
| 5,677,169 | 10/1997 | Ollar et al. | 435/287.9 |

*Primary Examiner*—Ralph Gitomer
*Attorney, Agent, or Firm*—David V. Padack; Eckert Seamans Cherin & Mellott, LLC

[57] ABSTRACT

A method for determining a sensitivity of a nonparaffinophilic hydrophobic microorganism to an antimicrobial agent. The method includes providing at least one receptacle containing an aqueous broth including a carbon source and introducing the nonparaffinophilic hydrophobic microorganism into the receptacle. The method further includes placing into the receptacle (i) a slide coated with a hydrophobic material and (ii) a predetermined quantity of the antimicrobial agent to be tested. By observing the nonparaffinophilic hydrophobic microorganism growth or lack thereof on the slide, it can be determined whether the predetermined quantity of the antimicrobial agent is effective in inhibiting growth of the nonparaffinophilic hydrophobic microorganism on the slide. An associated apparatus is also disclosed.

4 Claims, 1 Drawing Sheet

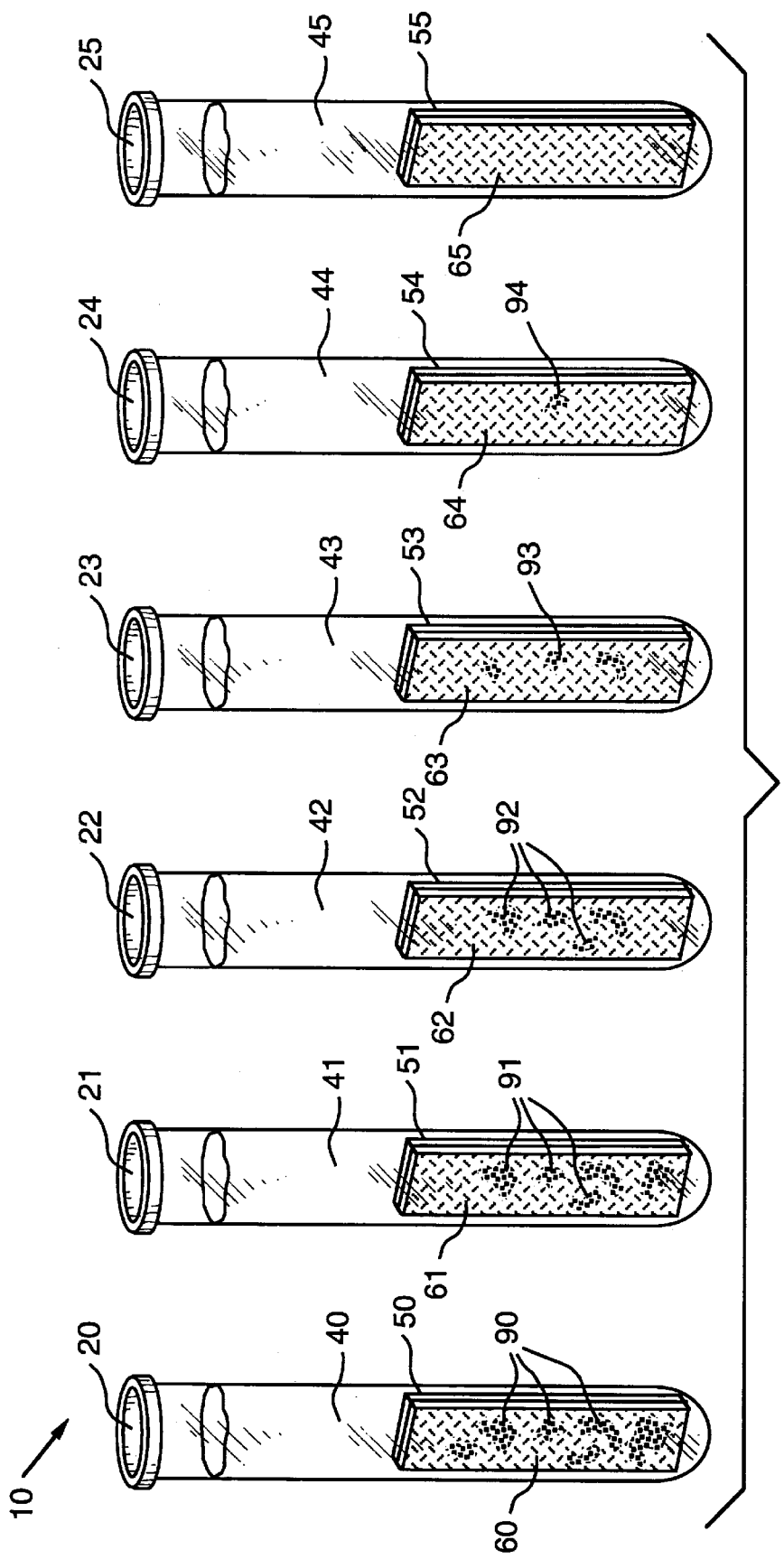

METHOD FOR DETERMINING THE ANTIMICROBIAL AGENT SENSITIVITY OF A NONPARAFFINOPHILIC HYDROPHOBIC MICROORGANISM

BACKGROUND OF THE INVENTION

This invention relates to a method for determining the antimicrobial agent sensitivity of a nonparaffinophilic hydrophobic microorganism and an associated apparatus.

Treating infections very often involves educated guesses by medical personnel as to the nature of the microorganism involved and the correct antimicrobial agent and quantity thereof needed to effectively treat the microorganism present in the infected tissue. Medical personnel are acutely interested in rapidly ascertaining which antimicrobial agents, and which dosages, are necessary in order to assure effective inhibition of the growth of all microorganisms present in the patient.

Several of my United States Patents teach an effective, efficient and economical way for medical personnel to rapidly ascertain which antimicrobial agent and which dosage is necessary in order to treat the patient. See U.S. Pat. No. 5,663,056, the disclosure of which is incorporated by reference herein. Despite the existence of this technology, there still remains a need to determine the antimicrobial agent sensitivity of nonparaffinophilic hydrophobic microorganisms.

SUMMARY OF THE INVENTION

The invention has met or exceeded the above-mentioned need as well as others. The method for determining the sensitivity of hydrophobic nonparaffinophilic microorganism to an antimicrobial agent and comprises providing at least one receptacle containing an aqueous broth including a carbon source and introducing into the receptacle the nonparaffinophilic hydrophobic microorganism. The method further includes placing into the receptacle (i) a slide coated with a hydrophobic material and (ii) a predetermined quantity of the antimicrobial agent to be tested. By observing the nonparaffinophilic hydrophobic microorganism growth or lack thereof on the slide, it can be determined whether the predetermined quantity of the antimicrobial agent is effective in inhibiting growth of the nonparaffinophilic hydrophobic microorganism on the slide.

An associated apparatus is also disclosed. The apparatus comprises a receptacle adapted to contain an aqueous broth including a carbon source, an amount of antimicrobial agent to be tested and the nonparaffinophilic hydrophobic microorganism. The apparatus further includes a slide coated with a hydrophobic material, the slide being adapted to being placed in the receptacle. Again, observation of the growth of the nonparaffinophilic hydrophobic microorganism on the slide can be used to determine the concentration of the antimicrobial agent necessary to resist the nonparaffinophilic hydrophobic microorganism growth on the slide.

BRIEF DESCRIPTION OF THE DRAWING

A full understanding of the invention can be gained from the following detailed description of the invention when read in conjunction with the accompanying lone drawing which shows one embodiment of the antimicrobial agent sensitivity apparatus.

DETAILED DESCRIPTION

As used herein, the term "nonparaffinophilic hydrophobic microorganism" means a nonparaffinophilic microorganism that, when inoculated into an aqueous broth containing a dissolved carbon source, will prefer to grow upon a hydrophobic surface introduced into the broth as opposed to growing within the aqueous broth itself. Examples of such nonparaffinophilic hydrophobic microorganisms include, but are not limited to, the following: *M. tuberculosis* complex (*M. tuberculosis, M. bovis, M. africanum, M. microti*); *M. paratuberculosis; M. leprae; pseudomonads*; and *nocardial* species.

As used herein, the term "nonparaffinophilic microorganism" means any microorganism sustained by a carbon source other than paraffin. Also, as used herein, the term "patient" refers to a member of the animal kingdom, including human beings The method and apparatus of the invention provide an efficient, effective and economical way of determining the sensitivity of a nonparaffinophilic hydrophobic microorganism to different antimicrobial agents and predetermined quantities thereof. Referring now to the lone FIGURE, the antimicrobial agent sensitivity method will be explained with reference to one embodiment of the antimicrobial agent sensitivity apparatus 10. The apparatus 10 consists of six receptacles in the form of test tubes 20, 21, 22, 23, 24, 25 each containing an amount of an aqueous broth including a carbon source, such as Middlebrook 7H9 broth, 40, 41, 42, 43, 44, 45. The aqueous broth in test tubes 21–25 contain uniform intervals of increasing concentrations of an antimicrobial agent to be tested. Test tube 20 is used as a control tube that does not contain any antimicrobial agent.

The nonparaffinophilic hydrophobic microorganism isolate is then introduced into each of the test tubes 20–25. This isolate can be obtained from a patient's body specimen. The body specimen can be sputum, fecal matter, cerebrospinal fluid, urine, gastric fluid, lymphatic material and purulent body fluids. These specimens can be obtained from the patient in the doctor's office or in the emergency room of a hospital, for example, by known techniques.

Slides 50, 51, 52, 53, 54 and 55 are coated with a hydrophobic material (defined further below) 60, 61, 62, 63, 64 and 65 (shown in partial cutaway sections on each slide), respectively, are then placed into respective test tubes 20, 21, 22, 23, 24 and 25. The slides are incubated for a period of a minimum of twenty-four (24) hours and possibly from 5 to 20 days. By observing nonparaffinophilic hydrophobic microorganism growth 90, 91, 92, 93, 94 on the slides 50–54, the minimum inhibitory concentration ("MIC") of the antimicrobial agent necessary to prevent nonparaffinophilic hydrophobic microorganism growth can be determined. In this case, hydrophobic material 65 coated on slide 55 has no nonparaffinophilic hydrophobic microorganism growth, thus the MIC concentration is found in test tube 55.

It will be appreciated that although apparatus 10 is shown with multiple receptacles and multiple slides 50–55, that the invention is not limited to multiple receptacles and multiple slides, but covers also a single receptacle and a single slide.

The hydrophobic materials that can be used are paraffin wax and other waxes; plastics such as polypropylene, polyethylene, polystyrene and tetrafluoroethylene; or silicones.

The invention utilizes the inventor's unexpected finding that *M. tuberculosis* and *M. paratuberculosis* and other microorganisms were able to grow on paraffin wax or other hydrophobic material in a broth media containing a dissolved carbon source, such as Middlebrook 7H9 broth. The waxy cell walls of these microorganisms, it is thought, favors attachment to a hydrophobic surface, such as paraffin wax, and thus the microorganism can imbibe the nutrients in the broth while being attached to the paraffin wax. This so-called "hydrophobic baiting" can be used to determine the antimicrobial agent sensitivity of these nonparaffinophilic hydrophobic microorganisms.

EXAMPLE

A patient is determined to have *M. tuberculosis* and the doctor wants to determine the appropriate dosage of the antimicrobial agent streptomycin. The *M. tuberculosis* isolate from the body specimen of the patient is introduced into receptacles 20–25 containing (1) the aqueous Middlebrook 7H9 broth and (2) the slide 50–55 containing the hydrophobic coating material. The following amounts of streptomycin are introduced into each receptacle.

| Receptacle | Amount |
| --- | --- |
| 20 | 0 (Control) |
| 21 | 100 µg/ml |
| 22 | 325 µg/ml |
| 23 | 550 µg/ml |
| 24 | 775 µg/ml |
| 25 | 1000 µg/ml |

After an incubation period of between 7–60 days, there is growth on all slides except slide 25. Therefore, the MIC of the streptomycin is determined to be 1000 µg/ml.

It will be appreciated that a method and kit are provided to determine the antimicrobial agent sensitivity of a nonparaffinophilic hydrophobic microorganism. The method is simple and efficient and the kit itself is fairly inexpensive.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method for determining a sensitivity of a nonparaffinophilic hydrophobic microorganism to an antimicrobial agent, said method comprising:

providing at least one receptacle containing an aqueous broth including a carbon source;

introducing into said receptacle said nonparaffinophilic hydrophobic microorganism;

placing into said receptacle (i) a slide coated with a hydrophobic material selected from the croup consisting of waxes, silicones and plastics and (ii) a predetermined quantity of said antimicrobial agent; and observing said nonparaffinophilic hydrophobic microorganism growth or lack thereof on said slide to determine whether said predetermined quantity of said antimicrobial agent is effective in inhibiting growth of said nonparaffinophilic hydrophobic microorganism on said slide.

2. The method of claim 1, wherein said nonparaffinophilic hydrophobic microorganism is selected from the group consisting of *M. tuberculosis* complex, *M. paratuberculosis, M. leprae, pseudomonads,* and *nocardial* species.

3. The method of claim 1, wherein said hydrophobic material is paraffin wax.

4. The method of claim 1, including providing a plurality of receptacles each containing an aqueous broth including a carbon source;

introducing into each receptacle said nonparaffinophilic hydrophobic microorganism;

placing (i) a separate slide coated with a hydrophobic material selected from the group consisting of waxes, silicones and plastics and (ii) an amount of an antimicrobial agent to be tested in each said receptacle, each said receptacle containing a different predetermined quantity of said antimicrobial agent; and observing said nonparaffinophilic hydrophobic microorganism growth or lack thereof on said slides to determine the minimum inhibitory concentration of said antimicrobial agent to inhibit growth of said nonparaffinophilic hydrophobic microorganism.

\* \* \* \* \*